United States Patent

Shen Lo

[11] 4,127,872
[45] Nov. 28, 1978

[54] NOVEL AMINO SILOXANE LUBRICANTS
[75] Inventor: Elizabeth Shen Lo, Princeton, N.J.
[73] Assignee: RCA Corporation, New York, N.Y.
[21] Appl. No.: 775,161
[22] Filed: Mar. 7, 1977
[51] Int. Cl.$^2$ .............................................. C07F 7/10
[52] U.S. Cl. ........................... 358/128; 260/448.2 N
[58] Field of Search ................. 260/448.2 N; 358/128

[56] References Cited
U.S. PATENT DOCUMENTS

| | | | |
|---|---|---|---|
| 3,317,577 | 5/1967 | Ryan | 260/448.2 N |
| 3,460,981 | 8/1969 | Keil et al. | 260/448.2 N X |
| 3,794,736 | 2/1974 | Abbott et al. | 260/448.2 N X |

Primary Examiner—Paul F. Shaver
Attorney, Agent, or Firm—H. Christoffersen; Birgit E. Morris

[57] ABSTRACT

Novel siloxane lubricants of the formula

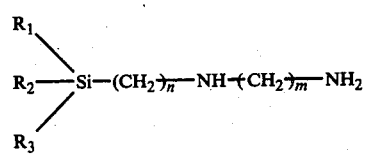

wherein $R_1$ is methyl or $(CH_3)_3$ SiO—, $R_2$ is methyl, $R_3$ is

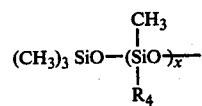

wherein $R_4$ is methyl or $-(CH_2)_n$ NH$-(CH_2)_m-$ NH$_2$, $n$ is an integer of at least 3, $m$ is an integer of at least 2 and $x$ can be 0 or an integer, and dimers thereof.

2 Claims, No Drawings

NOVEL AMINO SILOXANE LUBRICANTS

This invention relates to an improved lubricant for video discs. More particularly, this invention relates to amino alkyl siloxane lubricants which can be applied by evaporation.

BACKGROUND OF THE INVENTION

A novel video recording and playback system has been described by Clemens in U.S. Pat. No. 3,842,194 incorporated herein by reference. According to this system, disc replicas can be prepared having geometric variations in a spiral groove in the disc surface which correspond to capacitance variations representative of video signals. The conductive discs are coated with a thin dielectric coating. A metal stylus completes the capacitor and, during playback, rides upon the dielectric coating and detects dimensional variations in the groove. These variations are reconstituted in electrical signal form and converted back to video information suitable for display by a television receiver. The relief pattern and the grooves are of very small dimensions, on the order of 5,000 to 6,000 grooves per inch (12,700–15,240 grooves/cm). The disc is generally made of a plastic material, such as polyvinyl chloride, which is coated first with a thin conductive metal layer and then with a dielectric layer.

Stylus wear is one problem in this system. Since the stylus must be of very small dimensions to fit into the very small grooves, it is delicate and the friction caused during playback between the disc surface and the stylus tip tends to wear the stylus rapidly. Thus a lubricant layer is generally applied over the dielectric coating to reduce friction and consequent wear of the stylus.

A suitable lubricant for video disc replicas, in addition to imparting good lubricity to the disc surface, should have proper surface tension, should adhere to the disc surface, and should have proper cohesive and elastohydrodynamic properties so as to form a uniform, thin film which will support the stylus at a constant height above the signal elements during playback. In addition, the lubricant should be stable against degradation due to wear caused by repeated playbacks. The lubricant should also resist evaporation or changes in chemical or physical properties in ambient atmosphere for prolonged periods. It is further desirable that the lubricant be a good electrical insulator with a high dielectric strength. Still further, the lubricant should be chemically inert with respect to the material of the video disc replica itself, the conductive coating and the dielectric coating thereon.

One lubricant film that has been employed for the video disc heretofore, as disclosed by Kaplan and Matthies in U.S. Pat. No. 3,833,408, is a film of a methyl alkyl siloxane of the formula

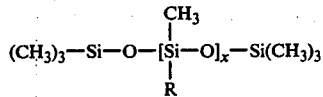

wherein R is an alkyl group of 4–20 carbon atoms and $x$ is an integer. These lubricants have the additional advantage that they can be vacuum evaporated onto the disc. This is desirable because the metal and dielectric films are conveniently applied in a vacuum chamber, see U.S. Pat. Nos. 3,843,399 and 3,982,066, and thus the lubricant films can be applied under vacuum as well.

However, the commercially available methyl alkyl siloxanes have proven to be somewhat less than ideal as far as wettability of the video disc surface is concerned. Thus it is difficult to prepare lubricant films of even thickness on the surface of the disc. Also, these lubricants tend to attract dust particles which strongly adhere to the disc surface and impede free passage of the stylus during playback. Other commercially available silicone oils and lubricants have also been tried, but most have severe drawbacks. One of the better oils in terms of properties is a siloxane oil of Dow Corning, XF4-3656, which has the basic structure

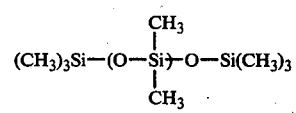

and contains about two percent by weight of an amine group

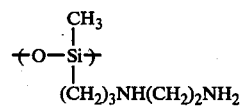

However, this siloxane cannot be evaporated and it hardens to a solid on standing after a short time.

A lubricant that fulfills all of the above requirements and in addition can be applied by evaporation, has improved wettability and is stable is desirable for the video disc application.

SUMMARY OF THE INVENTION

Novel lubricants of the formula

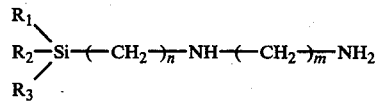

wherein $R_1$ is methyl or $(CH_3)_3 SiO-$, $R_2$ is methyl, $R_3$ is

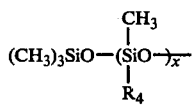

wherein $R_4$ is methyl or $-(CH_2)_n-NH-(-CH_2)_m-NH_2$, $n$ is an integer of at least 3, $m$ is an integer of at least 2 and $x$ can be 0 or an integer, and dimers thereof, are evaporable, wettable materials that are eminently suitable for use as video disc lubricants.

DETAILED DESCRIPTION OF THE INVENTION

The novel lubricants described herein are prepared in a two step process. A silicon hydride compound is first condensed with a halogen-1-olefin, according to equation (1)

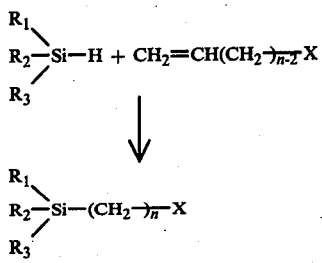
(1)

wherein R₁ to R₃ and n have the meanings given above and X is halogen, preferably chlorine or bromine. The silicon hydride starting materials are available from Silar Laboratories, Inc. of Scotia, New York and Petrarch Systems of Levittown, Pennsylvania.

The resultant siloxane is reacted with an alkylene diamine, as shown in equation (2)

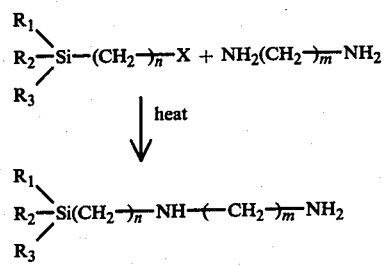
(2)

wherein $R_1$, $R_2$, $R_3$, X, n and m have the meanings given above.

The siloxane diamine products are distillable at about 5-50 microns pressure at temperatures of about 150-240° C.

Dimers of the above amino siloxanes can be obtained by fractional distillation.

The amino siloxanes of the invention can be applied as thin, conformal coatings on video discs by evaporation under vacuum or by spin coating from solution in a readily evaporable solvent. Discs coated with the present lubricants have improved playing characteristics as compared to prior art discs.

Since they are somewhat harder than prior art lubricants, they do not collect dust as readily. However, they are not as effective in their lubrication abilities after long term use.

The invention will be further described in the following examples, but it is to be understood that the invention is not meant to be limited to the details described therein.

EXAMPLE 1 — PART A

1-Hydroheptadecamethyloctasiloxane (29.6 grams) was charged to a reaction vessel fitted with a dropping funnel, a reflux condenser, thermometer, and stirrer and heated to 90° C. A catalyst solution (0.5 milliliter) containing 0.1 mol of chloroplatinic acid in isopropanol was added and 9 grams of 5-bromopentene-1 were added over a 20 minute period while maintaining the temperature between 90–110° C.

The unreacted bromide and isopropanol were removed by vacuum distillation at 90° C./8 mm and the product filtered.

A 97% yield (36 grams) of 5-bromopentylheptadecamethyloctasiloxane was obtained having a density of 0.9912 gram per milliliter (ml). The structure was confirmed by infra-red analysis and by elemental analysis: % Br found, 9.9; Theoretical, 10.8. The refractive index $n_D^{23}$ was 1.4180.

PART B

Twenty grams of the product of Part A was added to 8 grams of ethylenediamine at 80° C. while stirring. The temperature was raised to 90–100° C. for twenty minutes and cooled. Twenty ml of hexane were added, the organic layers separated, washed thoroughly with water and dried over calcium sulfate. The solvent was removed by distillation.

The product was distilled at 156° C. (30–50 microns) to yield 9.8 grams of 1-(5'-n-pentylamino-N-(2''-aminoethyl)-1,1,2,2,3,3,4,4,5,5,6,6,7,7,8,8,8-heptadecamethyloctasiloxane having the formula

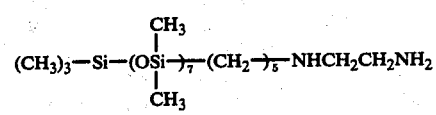

The structure was confirmed by elemental analysis: Theoretical: C, 40%; H, 9.4%; N, 3.8%; Found: C, 39.7%; H, 9.3%; N, 3.3% and by infrared analysis. The product had a viscosity at 25° C. of 10.5 centipoises (cps). The refractive index $n_D^{23}$ was 1.4201.

PART C

A portion of the product was fractionated by distillation. That portion distilling at 239° C./20 microns was collected and found to be the dimer having the formula

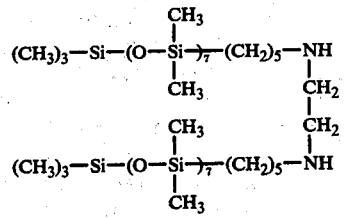

The structure was confirmed by elemental analysis: Theoretical N, 2.1%; Found, 1.8%. The refractive index $n_D^{23}$ was 1.4202.

EXAMPLE 2 — PART A

The procedure of Example 1 was followed except employing as the starting material bis(trimethylsiloxy)-dimethyl disiloxane (18.3 grams). After addition of the catalyst, 21 grams of 5-bromopentene-1 were added over 40 minutes.

An 86% yield (32.5 grams) of

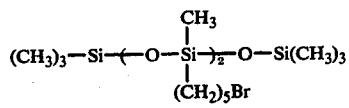

was obtained having a density of 1.127 grams per ml.

PART B

18 Grams of the product of Part A were added dropwise to ethylenediamine at 80° C. The procedure of Example 1 Part B was followed.

16.3 Grams (98% yield) of 3,5-bis-[5'-n-pentylamino-N-(2"-aminoethyl)]-1,1,3,5,7,7,7,-octamethyltetrasiloxane having the formula

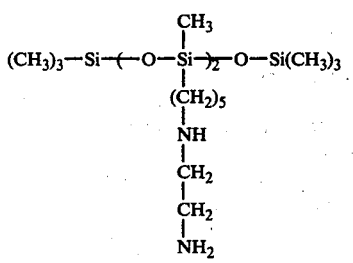

was obtained. The structure was confirmed by infrared analysis.

EXAMPLE 3 PART A

Following the procedure of Example 1 Part A, 20 grams of bis(trimethylsiloxy)methylsilane were reacted for two hours at 110° C. with 15 grams of 5-bromopentene-1 in the presence of 0.5 ml. of 0.1 Molar chloroplatinic acid in isopropanol. The product was filtered and distilled to remove unreacted bromide.

A 65% yield (18.8 grams) of a clear liquid product was obtained having a density of 1.0384 grams per ml. and a viscosity of 4.2 cps.

PART B

Eight grams of the product of Part A was added over a 20 minute period to 6 grams of ethylene diamine at 80° C. The reaction mixture was maintained at 90°-100° C. for 20 minutes longer, and ether was added to separate the product. The upper organic layer was collected, washed with water, dried over calcium sulphate and the solvent removed.

An 84% yield (6.3 grams) of 3-[5'-n-pentylamino-N-(2"-aminoethyl)]-1,1,1,3,5,5,5-heptamethyltrisiloxane having the formula

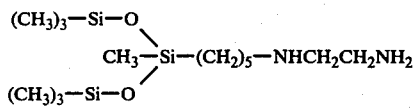

was obtained. The liquid product had a viscosity of 188 cps. The structure was confirmed by infrared analysis. The product was basic to pH paper.

EXAMPLE 4 — PART A

To 16.68 grams of bis(trimethylsiloxy)methylsilane heated to 120° C. was added 0.1 gram of chloroplatinic acid. Fifteen grams of 6-bromohexene-1 were added dropwise over a 30 minute period, maintaining the temperature at 110° C. After about 10 minutes, the temperature rose rapidly to 125° C. and the solution turned brown in color. After about 2 hours at 110° C., the solution was filtered. The solvent was removed under vacuum.

A yield of 87.2% (25.2 grams) of product was obtained.

PART B 23.6 grams of the product obtained in Part A was added dropwise to 20 ml. (17.6 grams) of ethylenediamine over a 5 minute period. The temperature was maintained at 70°-80° C. Heating was continued for 20 minutes longer. The reaction mixture separated into a clear top layer and a turbid lower layer. The top layer was collected and hexane was added to facilitate filtration. The solvent was then removed under vacuum.

An 80% yield of 3-[6'-n-hexylamino-N-(2"-aminoethyl)]-1,1,1,3,5,5,5-heptamethyltrisiloxane having the formula

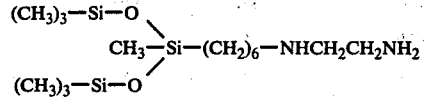

was obtained.

The product was distilled at 156° C./80 microns. 4.22 Grams of product having a viscosity of 8.8 cps. was obtained. The elemental analysis was:

Theoretical: C, 49.45; H, 10.99; N, 7.69; Found: C, 50.53; H, 10.96; N, 7.75

EXAMPLE 5

Lubricants of the invention were treated on standard video discs having a conductive metal layer and a glow discharged polystyrene layer thereon. The amino siloxanes were evaporated onto the polystyrene layer to a thickness of about 150-200 angstroms.

The discs were conditioned by first dropping 20 milligrams of vacuum cleaner dust evenly along the disc surface in a closed container and then storing for 18 hours at 85° F. and 90% relative humidity (RH). This is known as the hot, wet dust test.

The discs were then played while monitoring the number of incidents of poor signal, i.e., adding up the time during which the signal drops below 150 millivolts output. The first three plays were monitored, the discs were played 50 times more, and the next two plays monitored. Acceptable discs can have up to 6 seconds of poor signal in 30 minutes of play initially, and up to 9 seconds of poor signal in 30 minutes after 50 plays.

Table 1 below summarizes data obtained following the above hot, wet dust test for several of the compounds prepared above as well as for control compounds.

TABLE 1

| Lubricant Coating | Total time of poor signal | | | | |
| --- | --- | --- | --- | --- | --- |
| | Play 1, secs. | Play 2, secs. | Play 3, secs. | Play 54, secs. | Play 55, secs. |
| Example 1 Part A | 153[a] | 275[a] | 124[a] | 54[c] | 108[c] |
| Example 1 Part B | 7.6[a] | 0[a] | 0[a] | 0[c] | 0[c] |
| Example 1 Part C | 2.5[a] | 0.1[a] | 0.1[a] | 0[c] | 0[c] |
| Control SF 1147 | 3.2[b] | 1.0[b] | | | |
| Control XF 4-3656 | 5.3[b] | 0.4[b] | | | |

[a]counted for 10 minutes
[b]counted for 30 minutes
[c]counted for 3 minutes

EXAMPLE 6

Discs were coated with a lubricant of the invention as in Example 5 and conditioned by storing at 100° F. and 90% RH for 40 hours under clean conditions (high temperature, high humidity test), along with control samples. The discs were all preplayed for 5 minutes and then monitored for low signal as in Example 5, counting for 25 minutes of play. The data, based on an average of 6 discs for each group, are summarized below in Table II.

TABLE II

| Lubricant Coating | Total Time of Poor Signal | | |
|---|---|---|---|
| | Play 1, secs. | Play 2, secs. | Play 54, % less than 9 secs. |
| Example 1 Part B | 0.7 | 0.1 | 100 |
| Control SF-1147 | 7.7 | 3.2 | 87 |
| Control XF 4-3656, filtered | 187 | 257 | 100 |

I claim:

1. In information storage means adapted to provide capacitance variations through a pick-up means, said storage means comprising a conductive storage medium in which information is recorded in the form of geometric variations on a conductive surface thereof, a dielectric coating disposed over said conductive surface and a thin coating of a lubricant over said dielectric coating, the improvement wherein said lubricant is an aminosiloxane of the formula

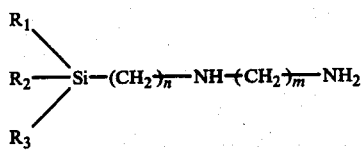

wherein $R_1$ is methyl or $(CH_3)_3 SiO-$, $R_2$ is methyl, $R_3$ is

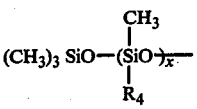

wherein $R_4$ is methyl or $-(CH_2)_n-NH-(CH_2)_m-NH_2$, $n$ is an integer of at least 3, $m$ is an integer of at least 2 and $x$ can be 0 or an integer, or dimers thereof.

2. In a capacitance video frequency recording means in the shape of a disc having a spiral groove on a face thereof and video information in the form of geometric variations in said groove, said disc having about 5,000 grooves per inch, said disc having a thin conductive layer on said face, a thin dielectric layer disposed over the conductive layer and a thin conformal coating of a lubricant disposed over the dielectric layer, the improvement wherein said lubricant is an aminosiloxane of the formula

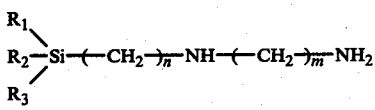

wherein $R_1$ is methyl or $(CH_3)_3 SiO-$, $R_2$ is methyl, $R_3$ is

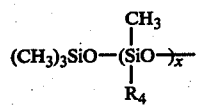

wherein $R_4$ is methyl or $-(CH_2)_n-NH-(CH_2)_m-NH_2$, $n$ is an integer of at least 3, $m$ is an integer of at least 2 and $x$ can be 0 or an integer, or dimers thereof.